United States Patent
Ariav

(10) Patent No.: US 6,856,141 B2
(45) Date of Patent: Feb. 15, 2005

(54) HIGH-PRECISION MEASURING METHOD AND APPARATUS

(75) Inventor: Arie Ariav, Doar Na Ashkelon (IL)

(73) Assignee: Nexense Ltd., Yavne (IL)

(*) Notice: Subject to any disclaimer, the term of this patent is extended or adjusted under 35 U.S.C. 154(b) by 56 days.

(21) Appl. No.: 10/615,952

(22) Filed: Jul. 10, 2003

(65) Prior Publication Data

US 2004/0104733 A1 Jun. 3, 2004

Related U.S. Application Data

(63) Continuation of application No. 09/983,430, filed on Oct. 24, 2001, now Pat. No. 6,621,278, which is a continuation-in-part of application No. PCT/IL00/00241, filed on Apr. 27, 2000.

(30) Foreign Application Priority Data

Apr. 28, 1999 (IL) .................................................. 129651

(51) Int. Cl.[7] .......................... G01R 27/04; G01R 27/32
(52) U.S. Cl. ...................... 324/639; 324/644; 324/637; 73/602; 342/86
(58) Field of Search ................................ 324/637–644; 73/597, 602; 342/86, 463

(56) References Cited

U.S. PATENT DOCUMENTS 4,315,260 A * 2/1982 Kupfer ........................ 342/86

* cited by examiner

Primary Examiner—Jay Patidar
Assistant Examiner—Vincent Q. Nguyen
(74) Attorney, Agent, or Firm—G.E. Erlich (1995) Ltd.

(57) ABSTRACT

A method and apparatus of measuring a predetermined parameter having a known relation to the transit time of movement of an energy wave through a medium, by transmitting from a first location in the medium a cyclically-repeating energy wave; receiving the cyclically-repeating energy wave at a second location in the medium; detecting a predetermined fiducial point in the cyclically-repeating energy wave received at the second location; continuously changing the frequency of transmission of the cyclically-repeating energy wave from the first location to the second location in accordance with the detected fiducial point of each received cyclically-repeating energy wave received at the second location such that the number of waves received at the second location from the first location is a whole integer; and utilizing the change in frequency to produce a measurement of the predetermined parameter.

16 Claims, 5 Drawing Sheets

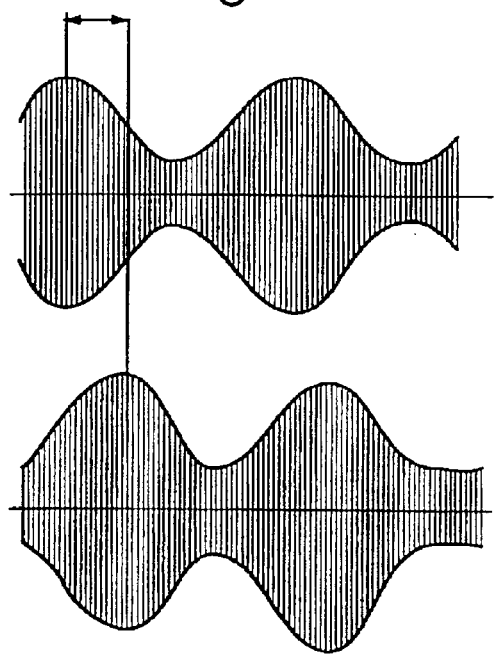
Fig. 8a
Fig. 8b
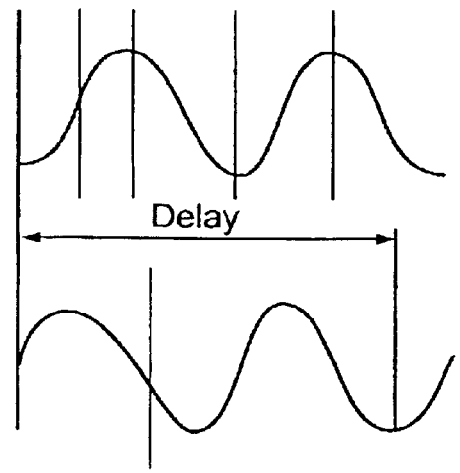
Fig. 8c
Fig. 8d
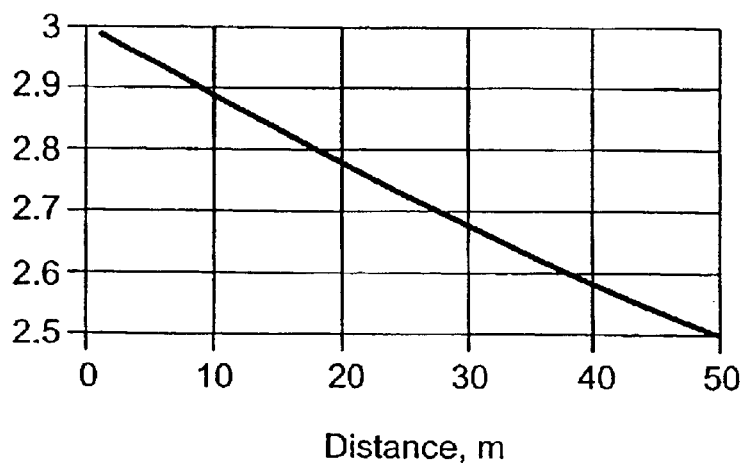
Fig. 9 ions in the system of FIG. 7; and

HIGH-PRECISION MEASURING METHOD AND APPARATUS

RELATED APPLICATIONS

The present application is a continuation of U.S. application Ser. No. 09/083,430 filed Oct. 24, 2001 now U.S. Pat. No. 6,621,278 which is a continuation-in-part of PCT/IL00/00241 having International Filing Dated Apr. 27, 2000 which claims priority from Israel Patent Application No. 129651 filed Apr. 28, 1999.

FIELD AND BACKGROUND OF THE INVENTION

Many measuring techniques are known for measuring distance, temperature, and other parameters, but such known techniques generally increase in expense according to the precision desired, and also generally have an upper limit as to the precision practically attainable by the technique. For example, to measure distances of meters or kilometers with a precision of microns or fractions of microns is extremely expensive, if attainable at all. The same limitations apply with respect to measuring temperature and other conditions.

OBJECTS AND BRIEF SUMMARY OF THE INVENTION

An object of the present invention is to provide a method and apparatus for measuring distances, temperatures, and a number of other parameters, in a manner which can be implemented with relatively low-cost equipment and with a very high degree of precision.

According to one aspect of the present invention, there is provided a method of measuring a predetermined parameter having a known relation to the transit time of movement of an energy wave through a medium, comprising: transmitting from a first location in the medium a cyclically-repeating energy wave; receiving the cyclically-repeating energy wave at a second location in the medium; detecting a predetermined fiducial point in the cyclically-repeating energy wave received at the second location; continuously changing the frequency of transmission of the cyclically-repeating energy wave from the first location to the second location in accordance with the detected fiducial point of each cyclically-repeating energy wave received at the second location such that the number of waves received at the second location from the first location is a whole integer; and utilizing the change in frequency to produce a measurement of the predetermined parameter.

As will be described more particularly below, the measurement may be the absolute value of the parameter, or merely the changes in the parameter during the measurement period. The description below sets forth a number of examples of parameters that can be measured with a high degree of precision, including distance, temperature, pressure, gaseous flow velocity, gaseous composition, etc., but it will be appreciated that the invention could be used in many other applications for measuring almost any parameter having a known relation to the transit time of movement of an energy wave through a medium, or for controlling a system according to the measured parameter. A number of applications of the invention, both in the medical field as well as in the industrial field, are described below for purposes of example.

In most of the applications described below, the cyclically-repeating energy wave transmitted by the transmitter is an acoustical (compressional) wave. However, the invention could also be implemented with electromagnetic waves, particularly in applications requiring the measurement of relatively large distances with a high degree of precision.

Further features and advantages of the invention will be apparent from the description below.

BRIEF DESCRIPTION OF THE DRAWINGS

The invention is herein described, by way of example only, with reference to the accompanying drawings, wherein:

FIG. 8 illustrates a series of waveforms at various locations in the system of FIG. 7; and FIG. 9 is a diagram helpful in explaining the system of FIG. 7.

DESCRIPTION OF PREFERRED EMBODIMENTS

Figure 1:
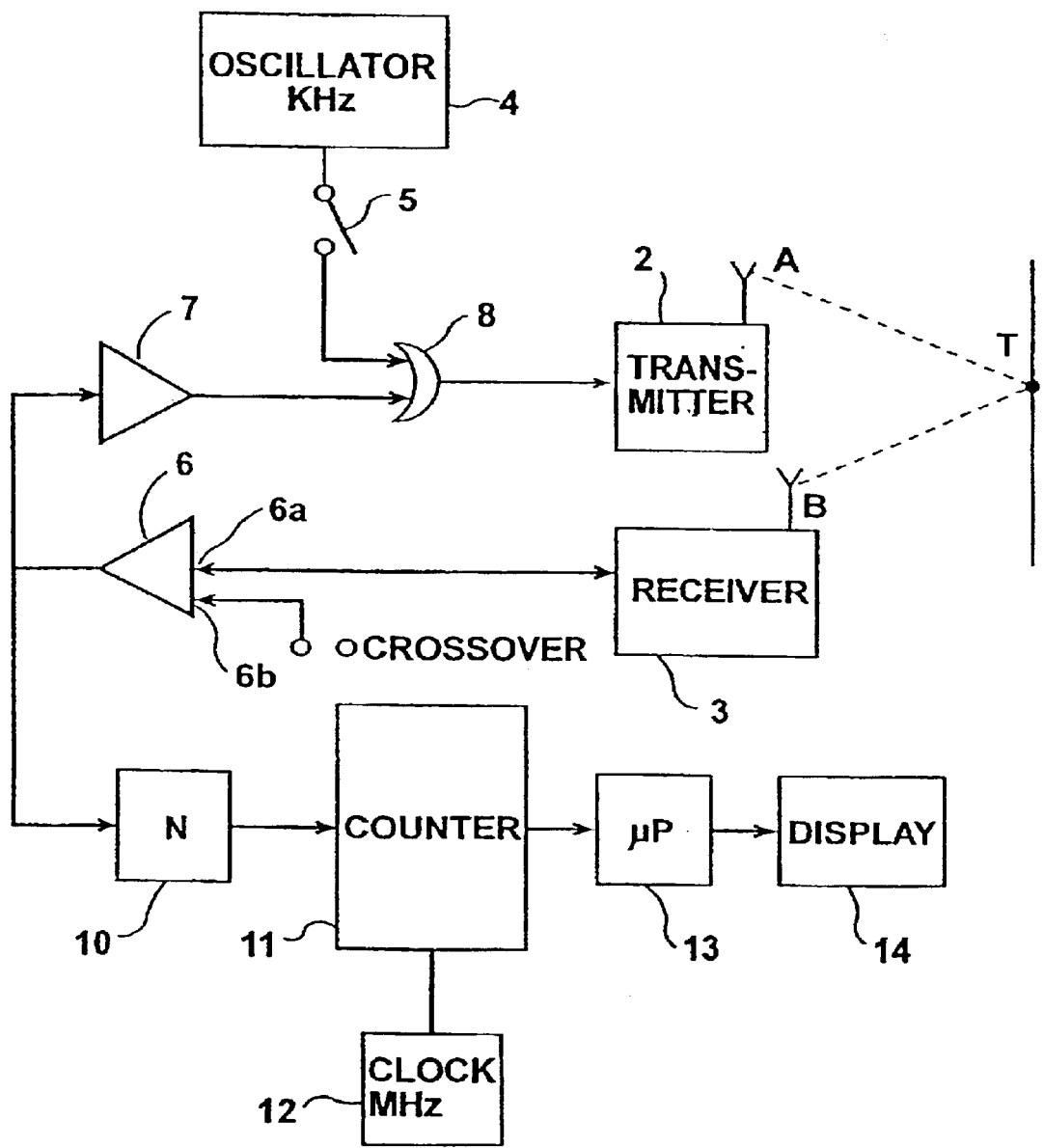
FIG. 1 is a block diagram illustrating one form of system constructed in accordance with the invention for measuring distances.

FIG. 1 is a block diagram illustrating a system for precisely measuring the distance to point T of a target or other object. The illustrated system is an echo system, and therefore the distance to target T is measured by measuring the transmit time taken by a cyclically-repeating energy wave transmitted at point A towards the target T until its echo is received at point B.

The system illustrated in FIG. 1 thus includes a transmitter 2 at location A for transmitting the cyclically-repeating energy wave towards target T, and a receiver 3 at location B for receiving the echo of the cyclically-repeating energy wave after reflection from target T. Initially, the energy wave is continuously transmitted from an oscillator 4 under the control of a switch 5 until the echoes are received by receiver 3; once the echoes are received, switch 5 is opened so that the received echo signals are then used for controlling the frequency of transmission of the cyclically-repeating energy wave by transmitter 2.

As shown in FIG. 1, the signals received by receiver 3 are fed to a comparator 6 via its input 6a. Comparator 6 includes a second input 6b connected to a predetermined bias so as to detect a predetermined fiducial or reference point in the received signal. In the example illustrated in FIG. 1, this predetermined fiducial point is the "zero" cross-over point of the received signal, and therefore input 6b is at a zero-bias. Other reference points could be used as the fiducial point, such as the maximum or minimum peak of the received signals.

The output of comparator 6 is fed to an amplifier or monostable oscillator 7 which is triggered to produce an output wave or signal for each fiducial point (zero cross-over point) in the signals received by the receiver 3. The signals from amplifier 7 are fed via an OR-gate 8 to the transmitter 2. OR-gate 8 also receives the output from oscillator 4 when switch 5 is closed.

Switch 5 is opened when the transmitter 2 receives a continuous stream of signals from amplifier 7 via OR-gate 8. When switch 5 is opened, transmitter 2 will thus transmit at a frequency determined by the fiducial points in the reflected signals received by receiver 3 and detected by comparator 6 to control amplifier 7. Accordingly the frequency of transmission by transmitter 2 will be such that the number of waves of the cyclically-repeating energy wave transmitted from location A and received in location B will be a whole integer.

It will thus be seen that while the frequency of the transmitter 2 will change with a change in the distance to the target point T, the number of wavelengths ($\lambda$) in the signal transmitted from the transmitter 2 to the target T, and reflected back to the receiver 3, will remain a whole integer. This is because the transmitter 2 transmissions are controlled by the fiducial points (zero cross-over points) of the signals received by receiver 3. This change in frequency by the transmitter 2, while maintaining the number of waves between the transmitter and receiver to be a whole integer, enables a precise determination to be made of the distance to the target point T. Thus, as known:

$F=C/\lambda$

Where: F and C are the frequency and velocity, respectively, of the cyclically-repeating energy wave in the respective medium; and $\lambda_L$ is the wavelength. For example, if the energy wave is an acoustical wave, and the medium is air under normal temperatures and pressures, C=340,000 mm/sec. Accordingly, if F=34 KHz, then $\lambda$–10 mm.

Assuming the initial transmit path ATB (FIG. 1) is 100 mm, it will be seen that the number of wavelengths in this transit path will be 10.

Now assuming that the transit distance ATB is increased by 1 mm, i.e., from 100 mm to 101 mm. While this transit distance is now increased from 100 mm to 101 mm, the transit time ATB will also be increased. However, since the frequency of transmitter 2 is controlled by the fiducial point of the signals received by receiver 3, the transmitter 2 will still produce the same number of Assuming that the initial transit distance ATB is 136 mm, and that the initial frequency (of source 4) is 500 KHz, the initial wavelength ($\lambda$) will be 340,000/500,000, or 0.68 mm; thus initially there will be 136/0.68, or 200 wavelengths in the transit path ATB.

If this transit distance ATB is increased by 1 micron, to 136.001 mm, the number of wavelengths will remain the same (200) as described above. Therefore the wavelength will be increased from 0.68 mm to 0.680005 mm (136.001/200); and the frequency of transmission by transmitter 2 will be decreased from 500 KHz to 499.9963236 KHz.

Assuming that clock 12 is a 500 MHz clock, the value outputted by counter 11 before the distance change will be $500 \cdot 10^6 / 500 \cdot 10^3$, or 1000.

After the distance change, the frequency of the transmitter 2 will be changed from 500 KHz to 499.996 KHz (340,000/0.680005).

The value of the counter for one clock period of 550 KHz will therefore be 1,000.0073 (500 MHz/499.996 KHz), or 0.0073 Hz difference from the initial frequency. The frequency difference of 0.0073 Hz is practically not measurable.

However, if the summation factor "N" of counter 10 is selected to be 1000, this difference of 0.0073 is multiplied by 1000, so that the difference now becomes 7.3 Hz, which is measurable as a practical matter. If "N" of counter 10 is selected to be 10,000, then this value of 0.0073 is multiplied by 10,000, so that the frequency difference now becomes 73 Hz, which is even more precisely measurable. waves during this increased transit time, and therefore the waves will be slightly increased in length. Thus, the increased wavelength will be 101/10=10.1 mm. The frequency of transmitter 2 will therefore be changed from 34 KHz to 340,000/10.1=33,663 KHz.

The frequency will thus be decreased by 337 Hz when the distance is increased by 1 mm. Such a frequency change can be easily measured. However, if the distance is changed by 0.001 mm (rather than 1 mm), the frequency change will be 0.337 Hz, which would be extremely difficult, if possible at all, to measure in a practical manner. However, such a small frequency change can be easily measured in the system illustrated in FIG. 1 by including a summing circuit which continuously sums the measured frequency changes over a predetermined time, e.g., 100, 1,000, 10,000, or more cycles, and produces periodic read outs of the summed changes.

Thus, the zero cross-over points detected in comparator 6, which are used for controlling the frequency of the transmitter 2, are also fed to a counter 10 to be counted "N" times, and the output is fed to another counter 11 controlled by a clock 12. Counter 11 produces an output to a microprocessor 13 which performs the computations according to the parameter to be detected or measured, and a display 14 which displays the output of the microprocessor.

The following example will illustrate the high precision capability of the described system.

The summations factor "N" can be determined according to the number of readouts/second required for any particular application. For example, if 100 readouts/second are required, (i.e., a readout every 10 ms), "N" of counter 10 could be selected to be 5000, whereupon the 0.0073 Hz frequency difference per run would be multiplied by 5000, so as to be 36.5 Hz. It will thus be seen that the precision of the measurement can be preset, almost without limitation, by the selection of the appropriate clock rate for clock 12, and summation factor "N" for counter 10.

The output from counter 11 is fed to a microprocessor 13 which computes the desired parameter and displays it in display 14. In the above-described system of FIG. 1, the parameter computed is the change in the transit distance ATB. If desired, the actual distance can easily be computed, e.g., by multiplying the velocity of sound (C) by the transmit time.

It will thus be seen that the system illustrated in FIG. 1 may be used for precisely measuring not only distance, but any other parameter, such as temperature or pressure in a gaseous medium, having a known relation to the transmit time of movement of the energy wave through the medium. It will also be seen that this measurement may be merely the changes in the parameter during the measurement period, or the absolute value of the parameter at any instant during the measurement period.

Figure 2:
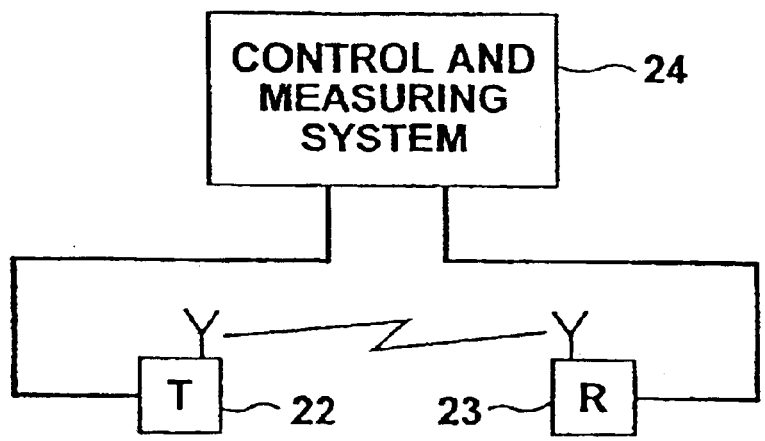
FIG. 2 is a block diagram illustrating the system of FIG. 1 but modified to receive the cyclically-repeating energy wave directly, rather than the echoes thereof.

FIG. 2 illustrates a modification in the system of FIG. 1, wherein the acoustical transmitter 22 transmits directly to the receiver 23, rather than by reflection, so that the parameter measured by the control and measuring system 24 will be the actual line-of-sight distance between the transmitter and receiver.

Figure 3:
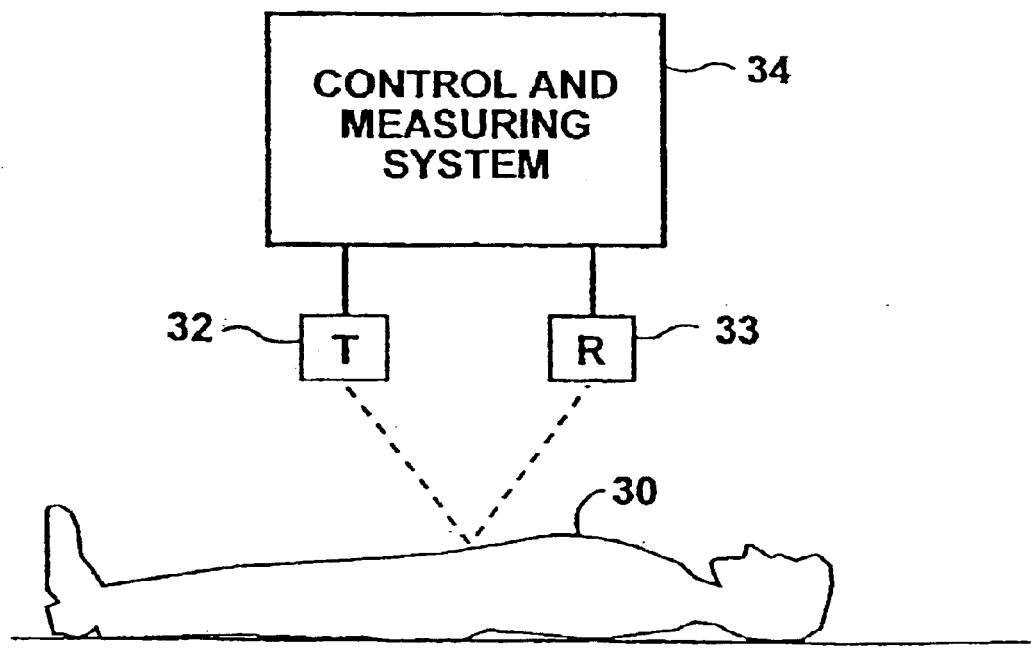
FIG. 3 is a block diagram illustrating the system of FIG. 1 implemented in medical apparatus for detecting and/or measuring diaphragm, chest or heart displacements of a patient in a real-time manner.

FIG. 3 illustrates an application of the invention for medical purposes, e.g., for heart and/or respiration monitoring of a person 30 under examination. Thus, an acoustical signal transmitter 32 is oriented to reflect the acoustical wave from a selected point on the person's body 30 to the receiver 33, so that the control and measuring system 34 will be able to detect, with a high degree of precision, any changes in position of the selected point on the person's body 30. The system of FIG. 3 may be used, for example, as a monitor for heart or respiration movements in a real-time manner, e.g., as an apnea detector or during surgery.

Figure 4:
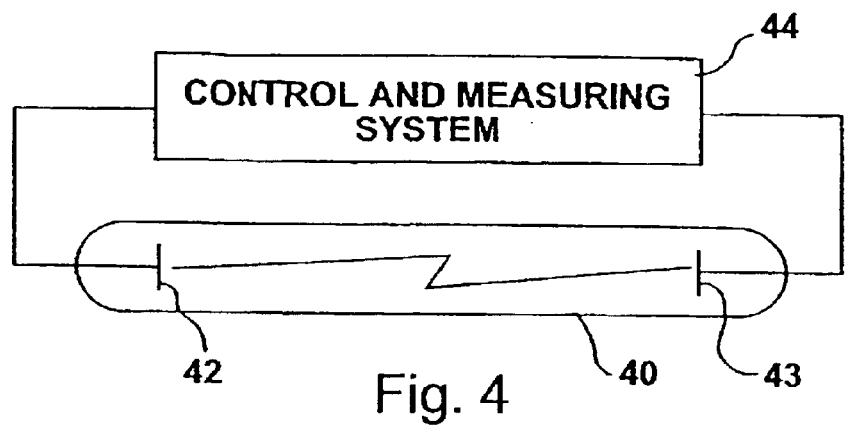
FIG. 4 is a block diagram illustrating the system of FIG. 1 for measuring temperature.

FIG. 4 illustrates the invention applied for precisely measuring temperature. Thus, the system illustrated in FIG. 4 includes an envelope 40 enclosing an acoustical transmitter 42 and a receiver 43 spaced therefrom by a gaseous medium, such as air at a known pressure. Since there is a known relationship between the temperature and the velocity of movement of an acoustical wave through a gaseous medium, the transmit time measuring system 44 in FIG. 4 would be able to compute the temperature of the gaseous medium within enclosure 40 with an extremely high degree of precision.

Figure 5:
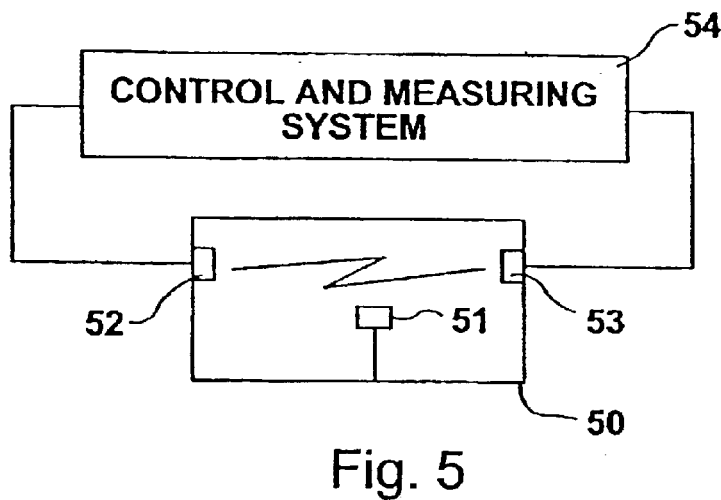
FIG. 5 is a block diagram illustrating the system of FIG. 1 for measuring a parameter, such as the temperature, pressure, or composition, of a gas within an enclosure, e.g., a reaction chamber for processing semiconductors.

FIG. 5 illustrates the invention implemented in a system for measuring the temperature within other types of endosures, such as a reaction chamber 50 for processing semiconductors 51. The acoustical signal transmitter 52 is at one side of the chamber, and the receiver 53 is at the opposite side, so that the control and measuring system 54 would be capable of measuring the temperature, temperature changes, or any other parameter within the reaction chamber 50 affecting the transmit time of movement of the acoustical wave from the transmitter 52 to the receiver 53.

Figure 6:
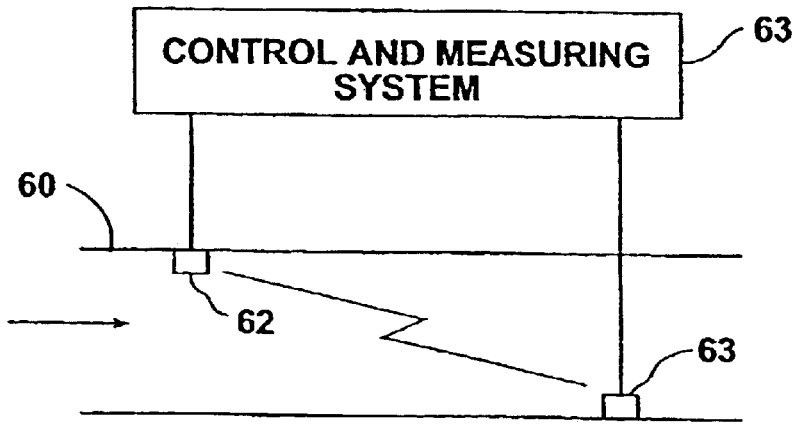
FIG. 6 is a block diagram illustrating the system of FIG. 1 for detecting or measuring a parameter in a flowing gas, such as the composition, velocity, or temperature of the flowing gas.

FIG. 6 illustrates the invention embodied in a system for measuring various parameters of a gaseous medium flowing with a conduit or other form of passageway 60. Thus, the acoustical signal transmitter 62 is at one side of the passageway, and the receiver 63 is located at a downstream point, preferably aligned with the transmitter 62 along a line which is oblique to the flow path of the gas through passageway 60. Such a device may thus be used for measuring: flow velocity, e.g., in accordance with the technique described in U.S. Pat. Nos. 4,425,805 or 4,914,959; molar mass or the composition of the gaseous mixture, e.g., as described in U.S. Pat. No. 5,645,071; metabolism, e.g., as described in U.S. Pat. No. 5,178,155; cardiac output of a subject, e.g., as described in U.S. Pat. No. 5,836,300, which patents are hereby incorporated by reference.

Many other applications of the invention can be made. Thus, because of the capability of measuring temperature in an extremely precise manner, the invention could be incorporated in a finger probe to measure cardiac output by first subjecting the finger to extreme cold, (e.g., by an ice pack), and then measuring the rate at which the body restores the finger to its normal body temperature which rate provides an indication of the body cardiac output. Another possible application is in an instrument for producing extremely-precise thermal scanning of industrial objects (e.g., vehicle engines), living beings, or body parts, (e.g., in a mammography for detecting cancer). Other medical applications include pregnant woman monitoring, heart, and respiration monitoring, etc. Further possible applications include measuring angular positions of a movable body, such as by measuring the angle of the liquid level with respect to a reference point on a container for the liquid. Other possible applications include geophones for detecting ground vibrations.

It will also be appreciated that the cyclically-repeating energy wave could be an electromagnetic wave, rather than an acoustical wave. Such applications would be particularly useful for measuring with high precision, large distances or movements of bodies at large distance from the measuring site.

Figure 7:
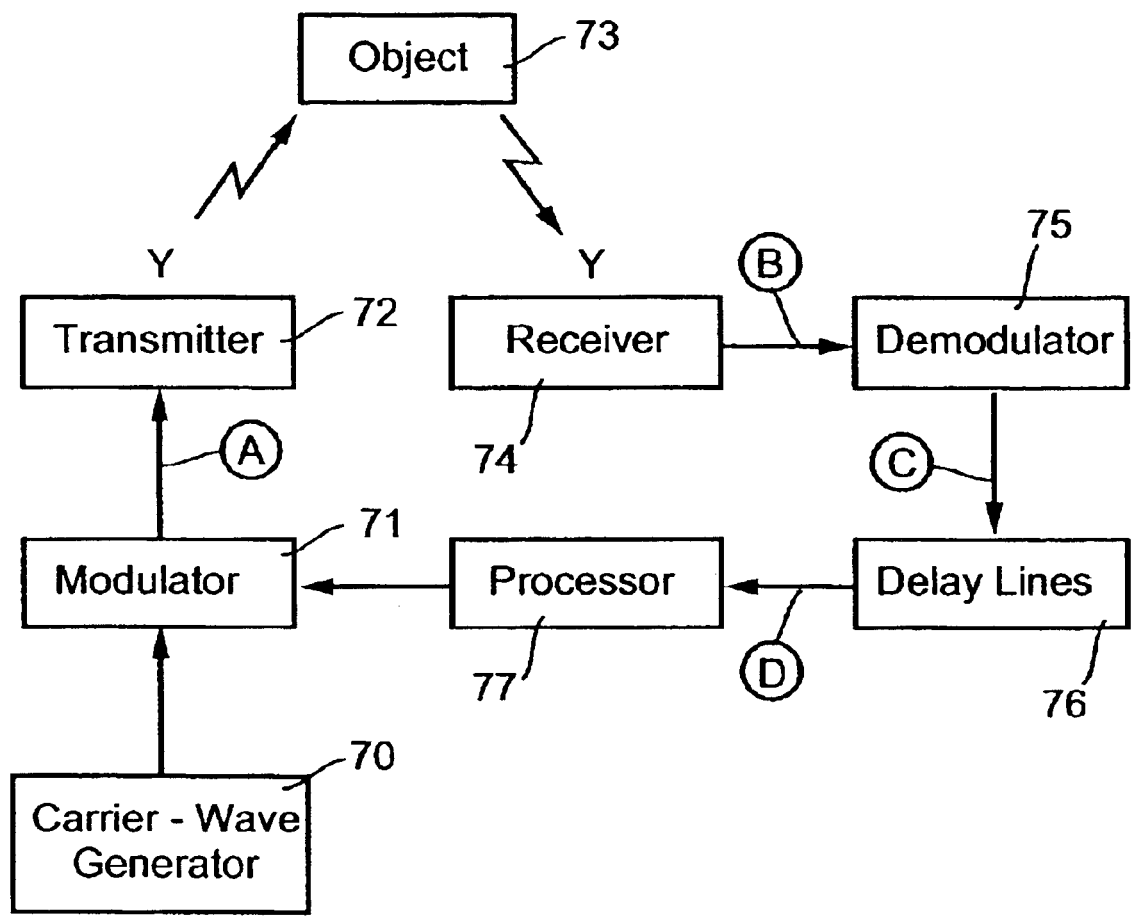
FIG. 7 is a block diagram illustrating the system of FIG. 1 applied with respect to an amplitude-modulated electromagnetic carrier wave.

FIG. 7 is a block diagram illustrating the invention implemented with respect to amplitude-modulated electromagnetic carrier waves, e.g., for measuring distance from an object. Such a system using very high carrier frequencies enables the use of compact, but narrow beam antennas or optical systems to be used for transmission and reception.

Thus, in the system of FIG. 7, the transmitter includes a generator 70 for generating a cyclically-repeating electromagnetic carrier wave, and a modulator 71 for amplitude-modulating the carrier wave by a cyclically-repeating electromagnetic modulating wave. The modulated carrier wave is transmitted by the transmitter 72 towards the object 73 whose distance is being measured.

The modulated carrier wave, after being reflected by the object 73, is received by a receiver 74 and demodulated by a demodulator 75 for separating the modulating wave from the received wave. In the illustrated system, there is further included a delay device 76, such as an acoustic delay line, for producing a phase shift of a whole-integer multiple in the separated modulating signal, before that signal is processed by the processor 77, in the manner described above, for detecting fiducial point of the received modulating signal and utilizing it for changing the frequency of the modulator 71 such that the number of modulating waves in the transmitted and received carrier wave is a whole integer.

Thus, the system illustrated in FIG. 7 provides feedback of the modulation frequency. The value of the modulation frequency will be set automatically so as to produce a phase shift in the feed-back loop which is a multiple of 360°. Thus:

$$fm = \frac{p}{\frac{2d}{c} + \frac{L}{v_S}}$$

where fm—modulation frequency,
  p—integer number,
  d—distance to obstacle,
  c—light velocity,
  L—length of delay line,
  $V_S$—sound velocity in delay line.

The provision of the acoustic delay line 76, which is optional, thus adds an artificial distance to the measurement, e.g., when measuring relatively short distances.

It will be appreciated that the carrier wave generator 70, and also the modulator 71, could operate at the radio frequency, infrared, or optical bands of the electromagnetic spectrum. For example, the generator 70 could be in the GHz range, and the modulator 71 could be in the MHz range. The delay line 76 could be an acoustic delay line. In this example, if the integer number (p) is equal to 5, the length of the delay line (L) would be 5 mm, and the sound velocity in the delay line ($v_S$) would be 5,000 m-sec.

FIG. 9 illustrates an example of the manner in which the modulation frequency (MHz) varies with the distance (m).

Many other variations, modifications and applications of the invention will be apparent.

What is claimed is:

1. A method of measuring a predetermined parameter having a known relation to the transit time of movement of an energy wave through a medium, comprising:

transmitting from a first location in said medium a cyclically-repeating energy wave;

receiving said cyclically-repeating energy wave at a second location in said medium;

detecting a predetermined fiducial point in the cyclically-repeating energy wave received at said second location;

continuously changing the frequency of transmission of the cyclically-repeating energy wave from said first location to said second location in accordance with the detected fiducial point of each received cyclically-repeating energy wave received at said second location by utilizing each detected fiducial point to trigger the transmission of said energy wave, such that the number of waves received at said second location from said first location is a whole integer;

and utilizing the change in frequency to produce a measurement of the transit time of the energy wave from said first location to said second location, and thereby, a measurement of said predetermined parameter.

2. The method according to claim 1, wherein said predetermined fiducial point is the zero cross-over point of the cyclically-repeating energy wave.

3. The method according to claim 1, wherein said changes in the frequency of said cyclically-repeating energy wave are measured by summing the changes in frequency over a predetermined number of cycles to increase the precision of said measurement.

4. The method according to claim 3, wherein the changes in frequency are summed over said predetermined number of cycles by measuring the changes in wavelengths of the cyclically-repeating energy wave in each cycle, and summing said changes in wavelength over said predetermined number of cycles.

5. Apparatus for measuring a predetermined parameter having a known relation to the transit time of movement of an energy wave through a medium, comprising:

a transmitter at a first location in said medium for transmitting a cyclically-repeating energy wave;

a receiver at a second location in said medium for receiving said cyclically-repeating energy wave;

and a processor for:

detecting a predetermined fiducial point in the cyclically-repeating energy wave received at said second location;

continuously changing the frequency of transmission of the cyclically-repeating energy wave from said first location to said second location in accordance with the detected fiducial point of each cyclically-repeating energy wave received at said second location by utilizing each detected fiducial point to trigger the transmitter, such that the number of waves received at said second location from said transmitter is a whole integer;

and utilizing the change in frequency to produce a measurement of the transit time of the energy wave from said first location to said second location, and thereby, a measurement of said predetermined parameter.

6. The apparatus according to claim 5, wherein said processor detects the zero cross-over point of each cyclically-repeating energy wave for continuously changing the frequency of transmission of the cyclically-repeating energy wave from said first location to said second location.

7. The apparatus according to claim 5, wherein said cyclically-repeating energy wave is a sinusoidal wave.

8. The apparatus according to claim 5, wherein said processor includes a summing circuit for continuously summing the changes in the measured parameter and for producing periodic readouts of the summed changes.

9. The apparatus according to claim 8, wherein said summing circuit includes a counter which counts the cyclically-repeating energy waves transmitted by the transmitter, and periodically reads out the count after a predetermined number of cycles.

10. The apparatus according to claim 5, wherein said receiver is located with respect to said transmitter so as to receive the echo of said cyclically-repeating energy wave after reflection from an object.

11. The apparatus according to claim 5, wherein said receiver is located with respect to said transmitter so as to directly receive said cyclically-repeating energy wave transmitted thereby.

12. The apparatus according to claim 5, wherein said transmitter transmits a cyclically-repeating acoustical wave.

13. The method according to claim 12, wherein said medium is a gaseous medium.

14. The apparatus according to claim 13, wherein said transmitter and receiver are enclosed within a common envelope, and are spaced from each other by said gaseous medium whose temperature is to be measured.

15. The apparatus according to claim 13, wherein said transmitter and receiver are located within a passageway through which the gaseous medium flows, and said processor produces a measurement of a parameter of the flowing gaseous medium.

16. A method of measuring a predetermined parameter having a known relation to the transit time of movement of an energy wave through a medium, comprising:

transmitting through said medium a cyclically-repeating energy wave;

receiving said cyclically-repeating energy wave transmitted through said medium;

detecting a predetermined fiducial point in the received cyclically-repeating energy wave;

continuously changing the frequency of transmission of the cyclically-repeating energy wave in accordance with the detected fiducial point of each received cyclically-repeating energy wave such that the number of waves received is a whole integer;

and utilizing the change in frequency to produce a measurement of said predetermined parameter.

* * * * *